(12) United States Patent
Hammond (10) Patent No.: US 9,968,374 B2
(45) Date of Patent: May 15, 2018

(54) METHOD AND INSTRUMENTS FOR PLACEMENT OF FLEXIBLE CANNULAE (71) Applicant: Jason Hammond, Reisterstown, MD (US)

(72) Inventor: Jason Hammond, Reisterstown, MD (US)

(*) Notice: Subject to any disclaimer, the term of this patent is extended or adjusted under 35 U.S.C. 154(b) by 0 days. days.

(21) Appl. No.: 15/561,794

(22) PCT Filed: Mar. 30, 2016

(86) PCT No.: PCT/US2016/025039
§ 371 (c)(1),
(2) Date: Sep. 26, 2017

(87) PCT Pub. No.: WO2016/161006
PCT Pub. Date: Oct. 6, 2016

(65) Prior Publication Data
US 2018/0078280 A1 Mar. 22, 2018

Related U.S. Application Data (60) Provisional application No. 62/142,361, filed on Apr. 2, 2015.

(51) Int. Cl.
*A61B 17/34* (2006.01)
*A61B 17/00* (2006.01)

(52) U.S. Cl.
CPC ...... *A61B 17/3415* (2013.01); *A61B 17/3423* (2013.01); *A61B 2017/00438* (2013.01); *A61B 2017/347* (2013.01); *A61B 2017/3456* (2013.01)

(58) Field of Classification Search
CPC ............ A61B 17/3415; A61B 17/3423; A61B 2017/3456; A61B 2017/347; A61B 2017/00438; A61B 2017/0042; A61B 17/3421
See application file for complete search history.

(56) References Cited

U.S. PATENT DOCUMENTS

| | | | |
|---|---|---|---|
| 5,295,950 A | 3/1994 | Ersek | |
| 5,300,082 A * | 4/1994 | Sharpe | A61B 17/0469 606/147 |
| 8,529,580 B1 | 9/2013 | Alshemari | |
| 2002/0058965 A1 | 5/2002 | Andrews | |
| 2009/0221968 A1 | 9/2009 | Morrison et al. | |
| 2014/0107685 A1* | 4/2014 | O'Neill | A61B 18/1445 606/170 |
| 2014/0128970 A1 | 5/2014 | Griffin et al. | |

OTHER PUBLICATIONS

Photographs (3 views) of Lufthansa plastic drink stirrer received between Mar. 19, 2016 and Mar. 29, 2016.

\* cited by examiner

*Primary Examiner* — Theodore Stigell
(74) *Attorney, Agent, or Firm* — Larson & Anderson, LLC (57) ABSTRACT

A cannula insertion device includes a rigid elongated body having a first end and a second end, an insertion tip located at a first end of the rigid elongated body, a cannula holder located along the rigid elongated body between the first and second ends, the cannula holder being configured to receive, hold, and release a cannula that is at least partially deformable; and a cannula insertion device control means located at a second end of the rigid elongated body. A system for facilitating access to a surgical site via minimally invasive means includes a cannula insertion device and a cannula having a deformable flange at one end.

15 Claims, 11 Drawing Sheets

METHOD AND INSTRUMENTS FOR PLACEMENT OF FLEXIBLE CANNULAE

CROSS-REFERENCE TO RELATED APPLICATIONS

This application claims the benefit of U.S. Provisional Patent Application No. 62/142,361, filed Apr. 2, 2015, the entire disclosure of which is incorporated by reference herein.

FIELD OF THE INVENTION

The present invention relates to methods and apparatus for surgical procedures.

BACKGROUND OF THE INVENTION

In less invasive surgical procedures, such as endoscopic or arthroscopic procedures, cannulas are inserted into portals to create a tunnel through which a surgical site can be accessed by a variety of surgical instruments. Some styles of cannula, such as flexible cannulas, including "button" style cannulas, solve many of the problems typically associated with rigid cannulas. Flexible button style cannulas, for example, consist of a flexible tube having flexible flanges at either end. Once these cannulas are inserted, the flanges hold the cannula in place and protect surrounding soft tissues from being damaged by the insertion, movement, and removal of instruments inserted into the body via the cannula. The flexibility of these cannulas allows for one or more flanges, when present as in a button style cannula, to lie flat against the inner tissues inside of the portal for the inner flange and against the skin for the outer flange. This keeps the inner portion of the cannula out of the way of surgical instruments, permitting unobstructed manipulation at the surgical site. Further, the flexibility of these cannulas makes manipulation of instruments at the surgical site easier, for example, by providing "give" when a surgeon has to lean or lever an instrument against the cannula when reaching at a difficult angle.

While these flexible button style cannulas offer significant advantages, they can be difficult to insert. Typically, this style of cannula is inserted by folding the interior flange, making a "taco" or "U" shape, and then using a curved hemostat to push the cannula into an existing portal. Friction from the portal often causes the cannula to slip out of the clamp, resulting in the cannula dislodging, and needing to re-start the insertion process. Successful insertion of the cannula requires that a surgeon identify the exact path or track of the original portal in as few attempts as possible, which can be difficult. Each unsuccessful attempt at insertion may cause additional subcutaneous and intramuscular tracks to develop, increasing the risk of water extravasation and damaging surrounding tissue. Extra attempts at insertion also increase surgical time and surgeon frustration. Further, multiple cannulas may be required if a cannula is damaged, dropped, or contaminated. The use of hemostats for insertion also presents some challenges. First, the portal skin incision needs to be longer to accommodate the increased bulk of the hemostat handles, which widen as they approach the finger loops. Second, because the portals used in less invasive surgical procedures are quite small, often on the scale of a few millimeters, it can be very difficult to open the clamped hemostat to release the cannula and place it in the portal. This becomes more problematic as the cannula increases in length. Finally, once the cannula is released from the hemostat clamp, the hemostat, which now located between the cannula and the perimeter of the portal, must be withdrawn from the portal without dislodging the cannula that is filling the portal. It can be difficult to withdraw the hemostat without dislodging the cannula.

In some cases, sutures may be passed through the cannula, and these sutures may be drawn or pulled into and through a first portal by a device that has an eyelet, clamp, or other means for securing the sutures to the device. This device is inserted through the joint via a second portal. The sutures are then pulled through the second portal, and can be tensioned, pulled, and used to manipulate the interior flange and position the cannula within the first portal. While this might be less traumatic to the soft tissue of the first portal and may result in easier placement of the cannula, it increases the minimum number of incisions/portals required to perform a procedure (at least 3 portals—1 portal for visualization, 1 portal for access with the clamp/eyelet device, 1 portal for cannula insertion, as opposed to 2 portals—1 portal for visualization, 1 portal for instrument access), increases surgical time by having to pass the suture in the cannula and making the extra portal that may otherwise be unnecessary, and increases cost because of the extra suture material required and increased surgical time.

In order to maximize the benefits flexible cannulas offer for both surgeons and patients, there exists a need for a more consistent, reliable, and less traumatic way to insert flexible cannulas.

SUMMARY OF THE INVENTION

The present invention provides a method and a plurality of instruments for inserting a flexible cannula, such as a button cannula, during a less invasive surgical procedure. The method and instruments provide for the insertion of a flexible cannula without creating extraneous subcutaneous and/or intramuscular tracks, and decreases the likelihood that the cannula will be dislodged from the portal during the placement procedure.

BRIEF DESCRIPTION OF THE DRAWINGS

FIG. 7 illustrates an exemplary blade type insertion device in accordance with the present invention.

DETAILED DESCRIPTION

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

The present invention provides a method and instruments to facilitate the insertion and placement of a flexible cannula for access to a surgery site in minimally invasive surgical techniques. The insertion devices of the present invention may include a conduit for a surgical guide, such as a guide wire, to accurately place the insertion devices in the original track created by the surgeon, and mechanisms to fold and lock the flexible cannula in place on the insertion device during the insertion procedure. The exemplary embodiments set forth herein are described with respect to the use of a flexible button type cannula. However, it should be appreciated that any type of at least partially flexible cannula may be used with the instruments and procedures described herein. For example, a button type cannula may have a relatively rigid neck, but have at least one flexible flange. Cannulae that are at least partially flexible and/or deformable shall be referred to herein as "flexible cannulae". The instruments described herein may be constructed of any material suitable for disposable or reusable surgical instruments including metals such as surgical grade steel alloys and titanium and titanium alloys, plastics such as polyether ether ketone (PEEK), or any combination thereof. It should also be appreciated that the instruments described herein should have sufficient rigidity along the length of the device to withstand the force required to insert a cannula into a portal, and may have at least some degree of flexibility at the insertion tip of the device to facilitate use of the device.

Tubular Insertion Device

Figure 1A:
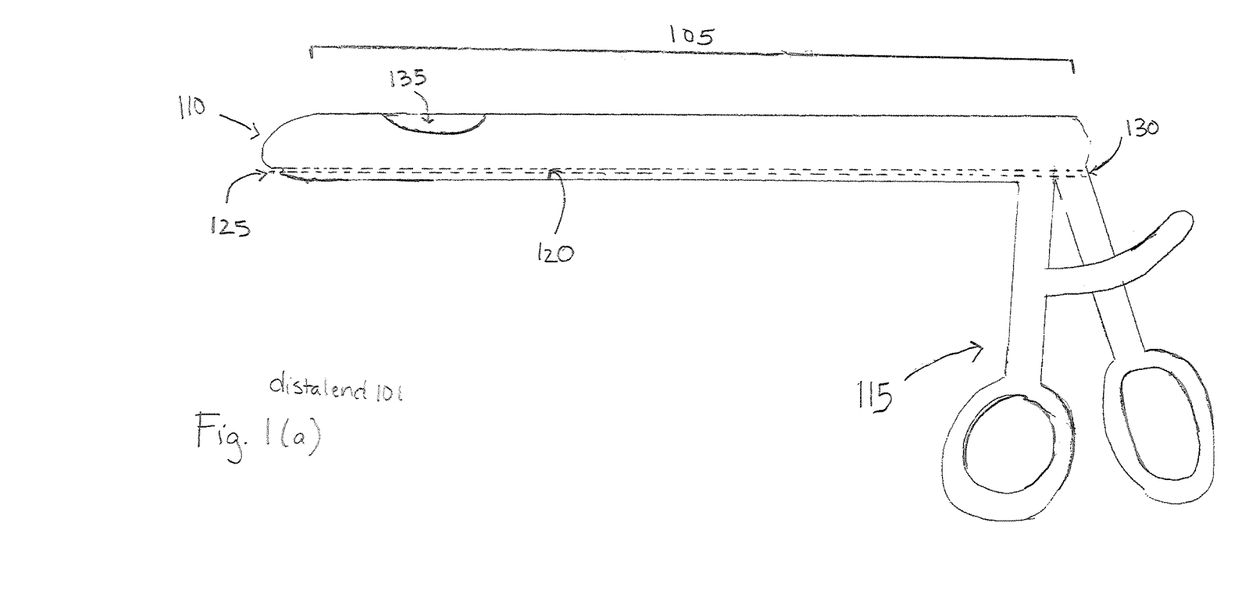
FIG. 1(a) illustrates a tubular insertion device in accordance with the present invention.

As shown in FIG. 1(a), in one embodiment, a tubular insertion device 100 in accordance with the present invention has a rigid, elongated body 105 having an insertion tip 110 at a distal end 101 and control means 115 at a proximal end 102. The elongated body 105 of the tubular insertion device 100 has a generally round, oval, or elliptical cross-section. In some embodiments, a conduit 120 is configured to receive a surgical guide, such as a guide wire. The conduit 120 runs along at least a portion of the length of the elongated body 105. The surgical guide is received in this conduit via an opening 125 in the insertion tip 110, and passes through the length of the elongated body 105, exiting the insertion device via an opening 130 at or near the proximal end of the insertion device. It should be appreciated that in use, as the insertion device is inserted through the portal, the surgical guide would advance through the conduit in the elongated body 105 and may be withdrawn via the conduit, or may be left in place to facilitate later aspects of the surgical procedure being performed. Preferably, opening 130 is configured and oriented such that, in use, the portion of the surgical guide that extends from opening 130 when the tubular insertion device is in use does not interfere with any control means 115 for the tubular insertion device.

Figure 1B:
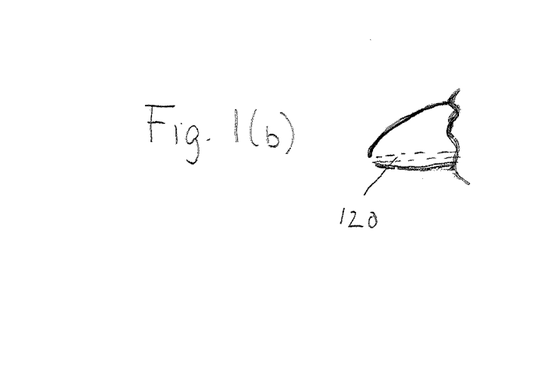
FIG. 1(b) illustrates an offset blunt insertion tip in accordance with the present invention.
Figure 1C:
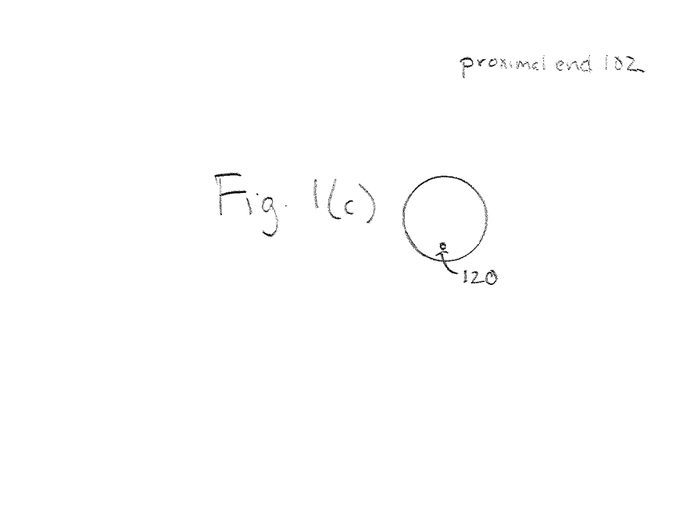
FIG. 1(c) illustrates a cross-section of a tubular insertion device configured to receive a surgical guide in accordance with the present invention.

The insertion tip 110 may be rigid or flexible, and may be tapered to a blunt end at the distal end 101 of the device (relative to the user) to facilitate insertion of the insertion device into a portal in a patient's body. In some embodiments, as shown in FIG. 1(a), the insertion tip is centrally located at the distal end of the insertion tip. In other embodiments, as shown in FIG. 1(b), the insertion tip is offset at the distal end of the insertion device. In either case, the tapered end facilitates gradual expansion of the portal as the insertion device is inserted into the portal, and minimizes trauma to surrounding tissues during insertion. In an exemplary embodiment, where the diameter of the elongated body is 10 mm, and the length of the elongated body of the inserter is 200 mm, the insertion tip begins to taper 5 mm proximal to the blunt end, and the diameter at the blunt end is 2 mm. It should be appreciated that these measurements are non-limiting, and may vary depending on a variety of variables including, but not limited to, the desired depth of placement of the cannula, the length and diameter of the cannula, the size of the original portal incision, and the size of the instruments to be inserted through the cannula.

A cannula holder 135 is located along the elongated body proximal to the insertion tip. The cannula holder may be any of the cannula holders described herein including, but not limited to, a slotted cannula holder, a pivoting cannula holder, a sliding cannula holder, or any combination thereof without departing from the scope of the invention. These various cannula holders are described in more detail in the various exemplary embodiments presented herein. "Opening" and "closing" of the cannula holder, when required is controlled by a user (surgeon) via any known control means suitable for control of a surgical instrument by a user during surgery. It should be appreciated that control means for the insertion device include, for example, racheting control mechanisms, known forceps and grasper control mechanisms, sliding control mechanisms, ergonomic grips and handles implemented at various angles relative to the elongated body of the insertion device in order to facilitate manipulation of the device, and the like. In some embodiments, the cannula holder may be fixed in one position and, therefore, the cannula holder is controlled by manipulating the insertion device control means. In other embodiments, the cannula holder may be manipulated, via a control means, between an "open" position and a "closed" position, including positions between open and closed. In still other embodiments, the cannula holder may be manipulated to a desired position, anywhere between "open" and closed" and fixed or secured at that desired position. The cannula holder may be fixed in position or manipulated by the user, for example, to adjust the size of the opening. Exemplary control means for the cannula holder include, but are not limited to, a sliding rod connected to the cannula holder, threaded rods (which may be controlled manually or via one or more motors), a ratchet mechanism or geared mechanism connected with at least one movable handle that allows for incremented advancement and retraction of the cannula holder, or any other mechanical means that can be used to adjust the size of the opening of the cannula holder. It should be appreciated that the various control means may also include features such as finger loops, thumb pads, grips, and the like to facilitate manipulation of the insertion device by the user. In some embodiments, the control means for the cannula holder may also serve as control means for the insertion device.

In a non-limiting example, as illustrated in FIG. 1(a), the control means 115 may be finger-loop ratcheting handles located at the proximal end of the insertion device. In some embodiments, the control means may include a lock mechanism which may be self-releasing or which may be released manually. Further, in some embodiments, a control means for both the insertion device and the cannula holder has two handles; one of which is stationary to facilitate manipulation of the entire insertion device, and the other handle being movable and permitting a user to manipulate the cannula holder between an open position and closed position. In some embodiments, the control means permit a user (surgeon) to control and vary the amount of tension placed on the portion of the cannula in contact with the cannula holder. In another embodiment, a control means has a thumb pad that is controlled by the thumb such that, when an overhand grip is placed on the handle the thumb can move the thumb control mechanism distal to release the restraint mechanism and proximal to secure it. In other embodiments, the control means may include one or more motors operable to open and close the cannula holder via input from an input device such as a track pad or joystick-style input device. In still other embodiments, the insertion device is adapted to be ergonomically grasped by the user and manipulated manually. It should be appreciated that any known control means for surgical tools or the like may be implemented for control of the cannula holder and the insertion device without departing from the scope of the invention. Further, the control means may be formed integrally with the insertion device and/or may be modular to be adapted for different users.

Slotted Cannula Holder

Figure 2A:
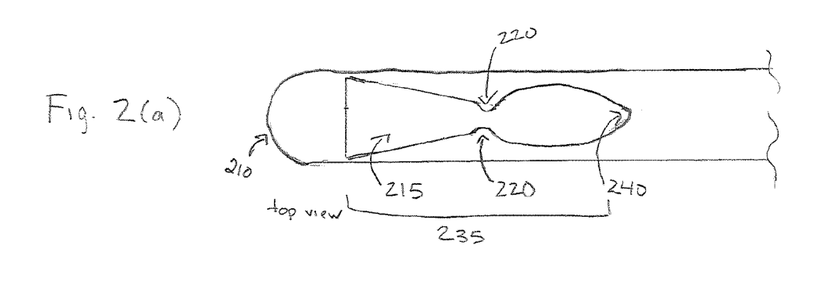
FIG. 2(a) illustrates a top view of a tubular insertion device having a slotted cannula holder in accordance with the present invention.

FIG. 2(a) illustrates a top view of a tubular insertion device having a slotted cannula holder 235 configured to receive a flexible cannula. In the context of a tubular inserter, a slotted cannula holder includes an opening or channel in the elongated body of the tubular insertion device that is configured to receive a flexible cannula. Preferably, the opening is slotted or elongated, for example, an oval, ellipsoid, triangular, bulbous, or teardrop shape. As illustrated in FIG. 2(a), a channel 215 is formed in the elongated body of the tubular insertion device proximal to the insertion tip. The insertion tip may be tapered and/or blunt, and may be centered or offset relative to the elongated body. The channel 215 is configured to receive the end of the flexible cannula that will be inserted through a portal incision and into a body. Channel 215 is accessible via a slotted opening in the elongated body. In some embodiments, the slotted opening gradually tapers, for example to a "U" or "V" shape, at one end, as illustrated in FIG. 2(a). In some embodiments, the slot-type opening may have one or more pairs of scallops or protrusions 220 (as shown in FIGS. 2(a) and 2(b)) along the length of the channel which slightly compress the neck of the cannula when the cannula is moved between the scalloped edges of the channel, to ensure that the cannula can be easily dislodged when desired.

Figures 2B, 2C:
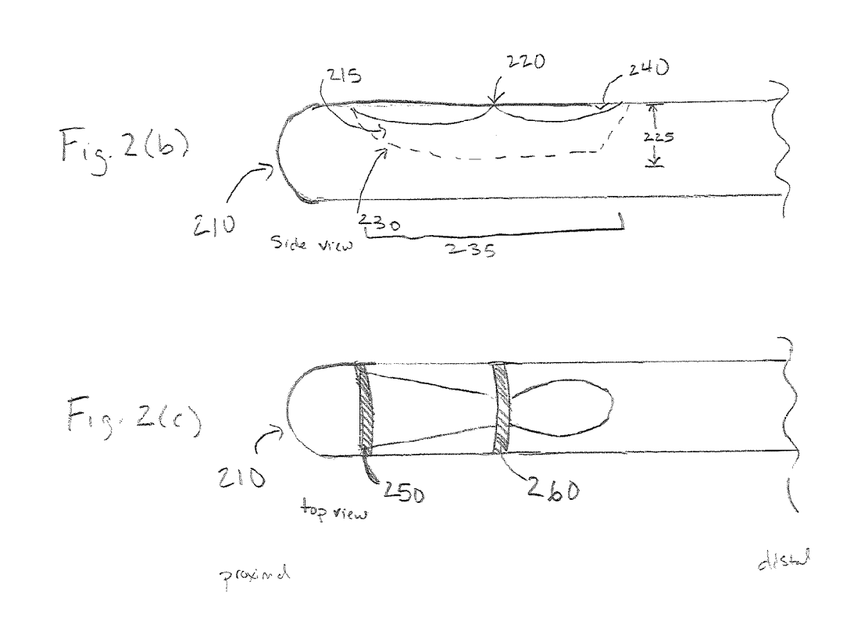
FIG. 2(b) illustrates a side view of tubular insertion device having a slotted cannula holder in accordance with the present invention.
FIG. 2(c) illustrates a top view of a tubular insertion device having a slotted cannula holder with a movable restraint mechanism in accordance with the present invention.

As illustrated in FIG. 2(b), the depth 225 of the channel is sufficient to accommodate the interior flange of the flexible cannula and, in some embodiments, a ramp 230 may be used to vary the depth of the channel. The ramp may be configured such that the depth of the channel increases along the length of the slot in the proximal direction, as illustrated in FIG. 2(b), may be configured such that the depth of the channel decreases along the length of the slot in the proximal direction, or multiple ramps may be implemented. In other embodiments, the depth of the channel is constant, and or may extend through the depth of the elongated body. In some embodiments, the channel may narrow as the depth increases to help "lock" the folded interior flange in place. In an exemplary implementation, for a flexible button cannula having a 8 mm diameter and a 25 mm flange, the slotted opening may be 6 mm in width, tapering to 2 mm at the proximal end, 25 mm long, and will gradually deepen to a depth of 7 mm along the length of the slot. It should be appreciated that these dimensions may vary depending upon the dimensions of the cannula to be used with the insertion instrument without departing from the scope of the invention. Preferably, the slotted opening is only slightly longer than the diameter of the flexible cannula or, in the case of a button style cannula, the diameter of the flange.

In some embodiments, the tapered end of the channel may include a locking mechanism for the neck of the cannula, referred to herein as a "V-lock." The interior portion of the V-lock 240, as illustrated in FIGS. 2(a) and 2(b), is preferably rounded or smoothed to minimize damage to the neck of the cannula when the neck of the cannula is held against it. In some embodiments, the depth of the channel extends beyond the tapered end of the V-lock, forming an overhang, as shown in FIG. 2. In other embodiments, the channel does not extend beyond the V-lock. In practice, with a cannula properly inserted, this permits the folded flange "taco" of the cannula to extend beyond the tapered end of the V-lock, so that the neck of the cannula can be snugged up against the tapered end of the V-lock, and securing the cannula in place.

In some embodiments at least a portion of the bottom of the channel may feature a rounded protrusion or bump to facilitate the folding of the flange (into a "taco" shape) or the end of the cannula. In some embodiments, this rounded protrusion may be formed by the top of the surgical guide conduit.

In some embodiments, the insertion device may also include a restraint mechanism mechanically connected to the control means to secure the cannula in place in the slotted cannula holder. The restraint mechanism may include a bar, curve, loop, catch ring or the like and advances from the distal end of the channel/slot to the proximal end of the channel/slot that is connected with a releasable mechanical mechanism and is controlled via the cannula holder control means at the proximal end of the insertion device. In another embodiment, the releasable mechanism may be a releasable lasso mechanism or spring-loaded ring configured to tighten around the neck of a cannula. As shown in FIG. 2(c), in the open position 250, the restraint mechanism is positioned near the distal end of the slot, or in another position that does not interfere with insertion of the cannula into the cannula holder. In the closed position 260, the releasable mechanical means is positioned towards the proximal end of the channel/slotted opening. The restraint mechanism may be slidably connected with the elongated body and is mechanically connected to a control means such as a sliding rod having a finger loop or thumb pad at the proximal end.

In still other embodiments, a slotted cannula holder may also have an ejection mechanism. The ejection mechanism may be, for example, a sliding or spring loaded mechanism proximal to the "V-Lock" or proximal end of the channel so that, upon appropriate manipulation of the cannula holder control means, the ejection means moves toward the distal end of the slot, forcing the cannula out of the slotted cannula holder.

To insert a flexible button style cannula using a tubular insertion device having a slotted cannula holder in accordance with the present invention, a surgical guide is placed in an incision using known methods, such as a cannulated switching stick. A flexible button style cannula is placed in the slotted opening of the tubular insertion device by folding the flange of the cannula, tucking it into the V-lock, and engaging the restraint mechanism (if included) via the cannula holder control means to advance the restraint mechanism such that it provides tension against the neck of the cannula to secure it into place. The surgical guide (if present) is then inserted into the conduit of the tubular insertion device, the insertion device is inserted into the portal to a desired depth, manipulated into position by the user, and then the releasable mechanism (if included) is released. Once the cannula is released from the insertion device (confirmed, for example, via a visualization device), the surgical guide and insertion device are removed, and the flexible cannula returns to its undeformed shape and fits snuggly against the tissues surrounding the portal.

Figure 3A:
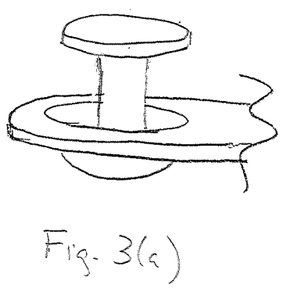
FIGS. 3(a)-3(d) illustrate the deformation of a flexible cannula relative to a slotted cannula holder in accordance with the present invention.
Figure 3B:
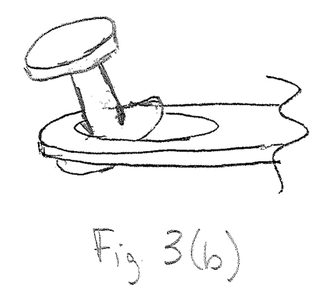
Figure 3C:
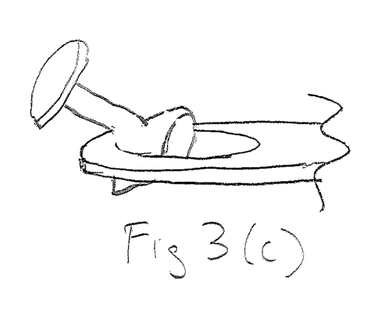
Figure 3D:
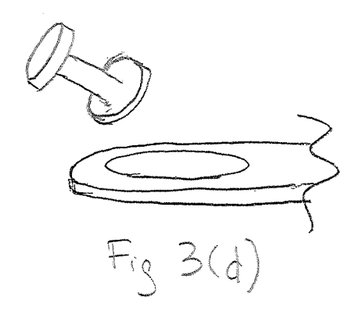
Figure 3E:
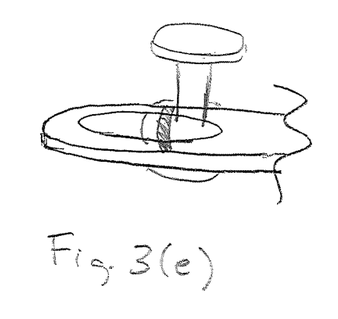
FIGS. 3(e) and 3(f) illustrate the deformation of a flexible cannula relative to a slotted cannula holder with a restraint mechanism in an insertion device in accordance with an embodiment of the present invention.
Figure 3F:
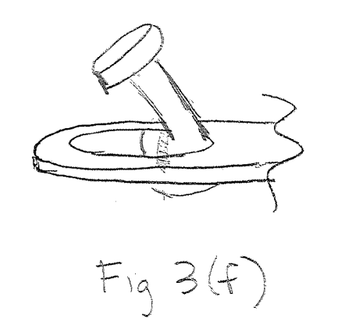

FIGS. 3(a)-3(d) illustrate the deformation of a flexible cannula relative to a slotted cannula holder in accordance with the present invention. In FIG. 3(a), the cannula is inserted into a slotted cannula holder of an insertion device in accordance with the present invention. In FIGS. 3(b) and 3(c), the deformation of the cannula as the insertion device is manipulated to release the cannula from the slotted cannula holder. FIG. 3(d) illustrates the cannula, which has returned to its original shape, as it is disengaged or released from the slotted cannula holder of an insertion device in accordance with the present invention. FIGS. 3(e) and 3(f) illustrate the deformation of a flexible cannula relative to a slotted cannula holder with a restraint mechanism in an insertion device in accordance with an embodiment of the present invention. FIGS. 3(e) and 3(f) illustrate the slight deformation of the neck of the cannula with the restraint mechanism engaged. This allows the cannula to be retained in the slotted cannula holder even when cannula itself is significantly deformed by other forces, as illustrated in FIG. 3(f).

Pivoting Cannula Holder

Figure 4:
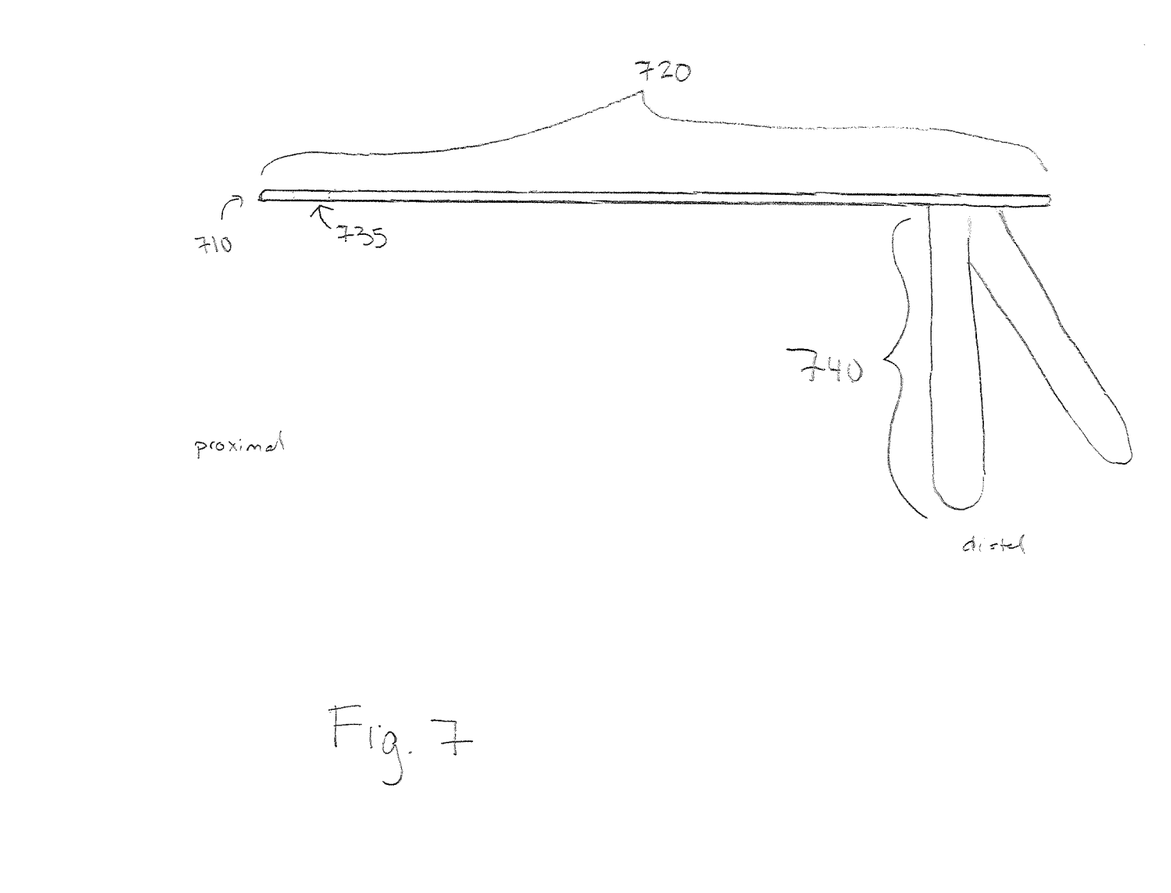
FIGS. 4(a)-4(d) illustrate tubular insertion devices having pivoting cannula holders in accordance with the present invention.
Figure 4A:
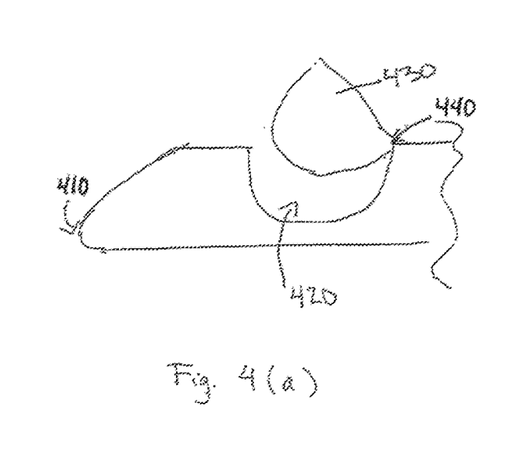
Figure 4B:
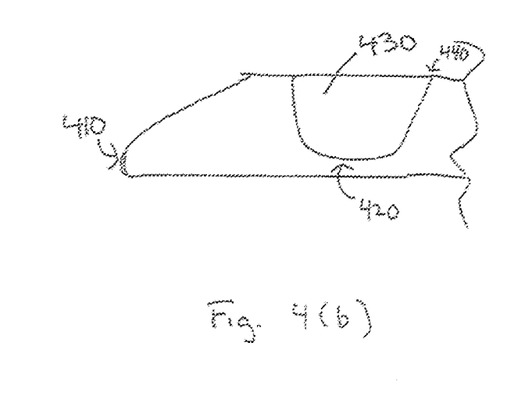
Figure 4C:
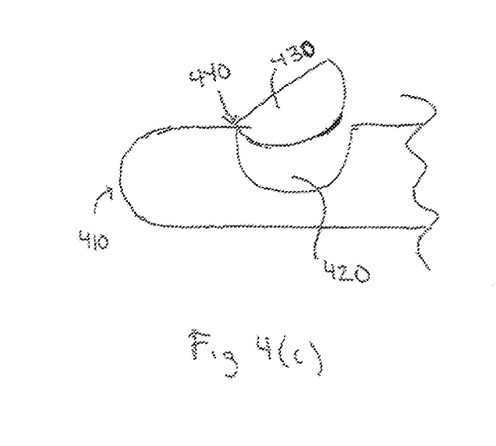
Figure 4D:
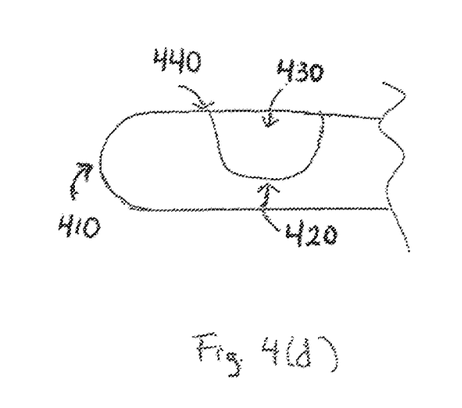

A pivoting cannula holder is located along the elongated body of the tubular insertion device, proximal to the blunt insertion tip. Exemplary tubular insertion devices having pivoting cannula holders are illustrated in FIGS. 4(a)-4(d). The insertion tip 410 may be centered, as illustrated in FIGS. 4(c) and 4(d), or offset, as illustrated in FIGS. 4(a) and 4(b). As described above, the insertion tip may be tapered and/or blunt. As shown in FIGS. 4(a)-4(d), a notch 420 is formed in the elongated tubular body. The notch may be partial depth (shown) or full depth. The notch preferably has sufficient depth to accommodate at least a portion of a flexible cannula intended to be inserted into a body. A door 430 is pivotably connected to the elongated tubular body at either the proximal end of the notch 420 (FIGS. 4(a) and 4(b)) or the distal end of the notch 420 (FIGS. 4(c) and 4(d)) via, for example, a hinge 440. The door may extend along the entire length of the notch, or may extend along a portion of the length of the notch. The pivotable connection and door are mechanically connected to the control means such that the door can be opened (as shown in FIGS. 4(a) and 4(c)) and closed (as shown in FIGS. 4(b) and 4(d)) via the control means. Preferably, the pivotable connection and control means are configured to allow the door to "open" fully to allow unobstructed access to the notch for placement of the "taco" folded, inside the end of the cannula, and allows for the user to vary the position of the door to increase or decrease tension on the neck of the cannula when the cannula is inserted in the cannula holder. In a non-limiting example, the position of the door may be controlled by one or more guy wires running through the center of the tubular cannula, the one or more guy wires being tensioned (or released) by a user via the control means, or may be fixed so that it holds the cannula in place by deforming the cannula. Preferably, the door should be curved, following the curvature of the circumference of the tubular cannula. In some embodiments, the door is configured such that it completely covers the width of the notch when the door is in the closed position. In other implementations, the door may be the width of only a portion of the notch.

In some implementations, the pivot point is located at the proximal end of the notch, and the notch and door extend in the distal direction to form at least a portion of the insertion tip.

Figure 5:
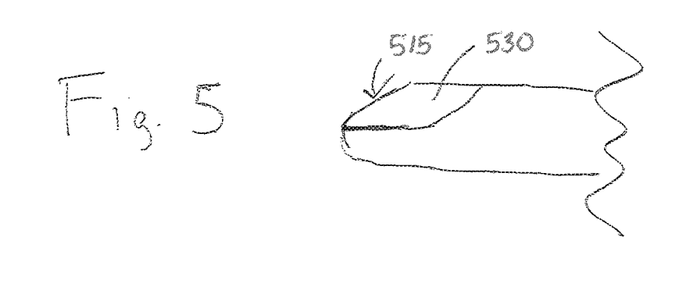
FIG. 5 illustrates a door having an opening to hold a cannula in accordance with the present invention.

As illustrated in FIGS. 5(a) and (b), the door may have a "V" or "U" shaped notch 515 at the opening end of door 530 to facilitate grasping of a cannula. In some implementations, the opening end of the door and/or the corresponding end of the notch may be textured, ramped, have "wings," or have an overhang (as described above) to facilitate folding and placement of the cannula in the cannula holder.

To insert a flexible button style cannula using a tubular insertion device having a pivoting cannula holder in accordance with the present invention, a surgical guide is placed in an incision using known methods, such as a cannulated switching stick. A flexible button style cannula is placed in the notch of the tubular insertion device by folding the flange of the cannula, tucking it into the notch of the cannula holder door, and using the control means to manipulate the door such that the door places tension on the neck and/or inner flange of the cannula. The surgical guide is then inserted into the conduit of the tubular insertion device, the insertion device is inserted into the portal to a desired depth, and then the door is opened via the control means. When the cannula is released from the insertion device (confirmed via a visualization device), the surgical guide and insertion device are removed, and the flexible cannula returns to its non-deformed shape and fits snuggly against the tissues surrounding the portal. It should be appreciated that, in some situations, it may be necessary to further manipulate the cannula before withdrawing the tubular insertion device. To accomplish this, a portion of the cannula may be grasped between the door and the notch by aligning a portion of the cannula with the notch in the insertion device, and then manipulating the door via the control means to place tension on the "caught" portion of the cannula.

Sliding Cannula Holder

Figures 6A, 6B:
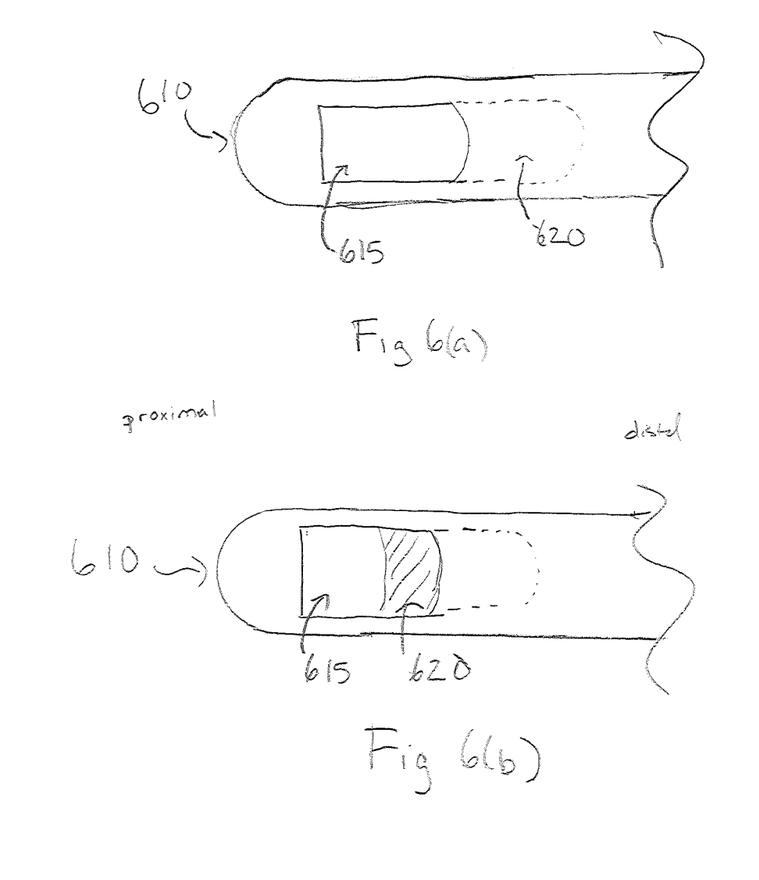
FIGS. 6(a) and 6(b) illustrate an insertion device having a sliding cannula holder in accordance with the present invention.
Figures 8A, 8B:
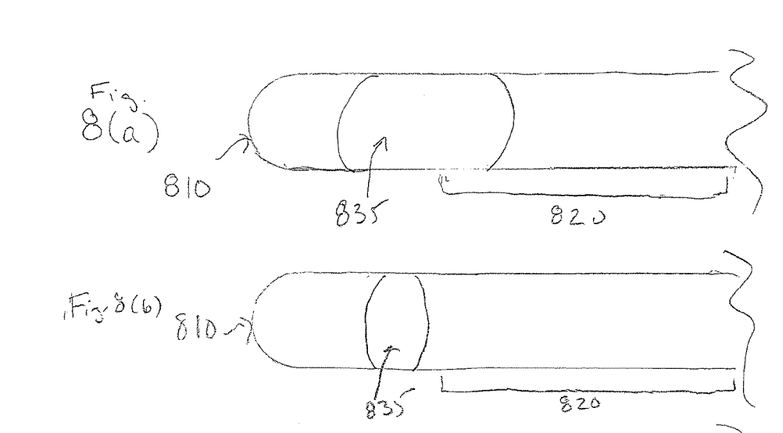
FIGS. 8(a)-8(d) illustrate a blade-type inserter having an adjustable slotted cannula holder in accordance with the present invention.
Figure 8C:
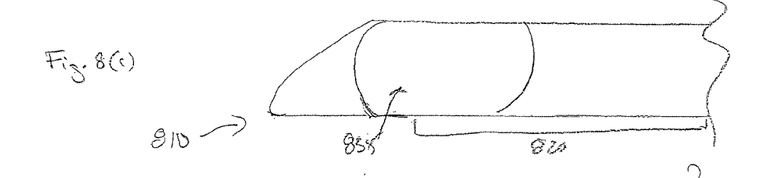
Figure 8D:
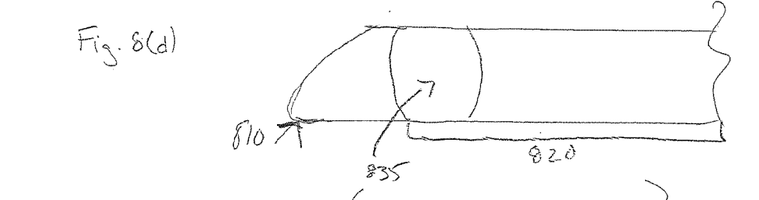
Figure 8E:
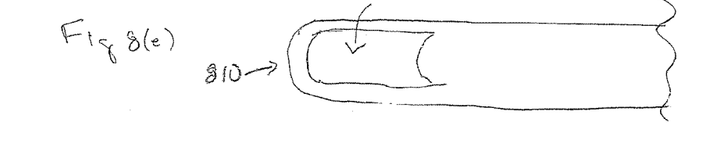
FIGS. 8(e) and 8(f) illustrate a blade-type inserter having a fixed slotted cannula holder in accordance with the present invention.
Figure 8F:
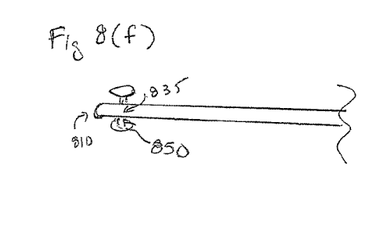
Figure 9A:
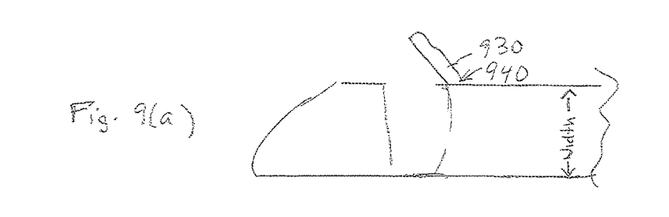
FIGS. 9(a)-9(f) and 10(a)-10(d) illustrate a blade-type inserter having a pivoting cannula holder in accordance with the present invention.
Figure 9B:
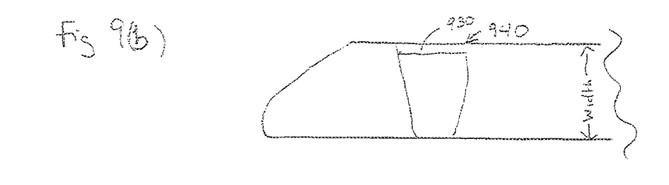
Figure 9C:
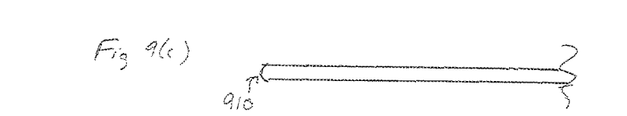
Figure 9D:
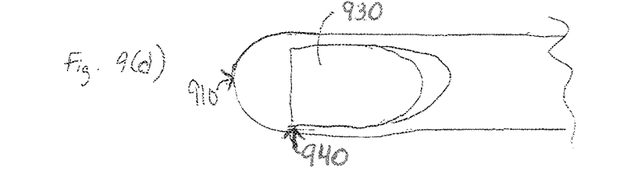
Figure 9E:
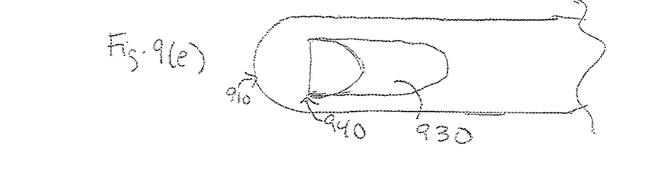
Figure 9F:
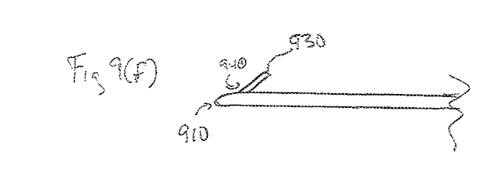
Figure 10A:
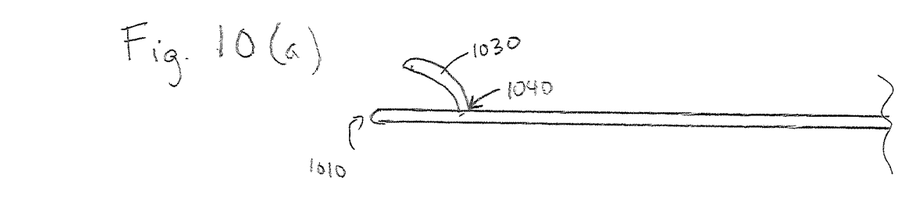
Figure 10B:
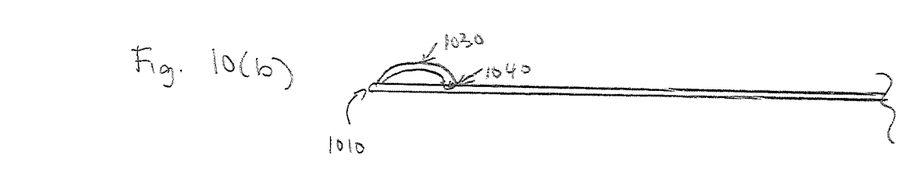
Figure 10C:
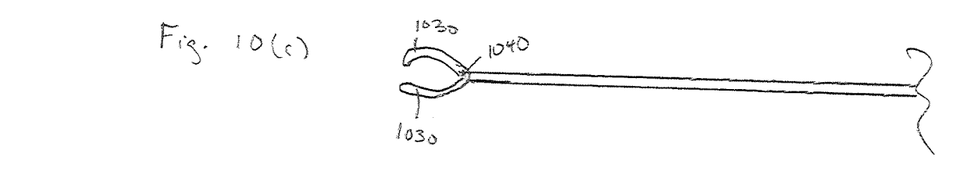
Figure 10D:
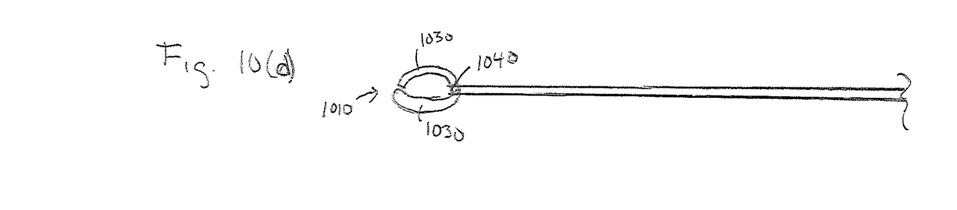

FIGS. 6(a) and 6(b) illustrate sliding cannula holder located along the elongated body of the tubular insertion device, proximal to the insertion tip 610, in accordance with the present invention. The insertion tip may be tapered and/or blunt, and may be centered or offset relative to the elongated body of the insertion device. As with the pivoting cannula holder, a notch 615 is formed in the elongated tubular body. This notch 615 may be partial-depth or full-depth. The notch preferably has sufficient depth to accommodate at least a portion of a flexible cannula intended to be inserted into a body. A door 620 is slidably connected to the elongated tubular body at either the proximal end of the notch 615 or the distal end of the notch (not shown). For example, in some embodiments, the sliding door may move along a track and be controlled by a control means such as a rod or guide wire that is used to manipulate the door along the length of the track. The door may extend along the entire length of the notch, or may extend along a portion of the length of the notch. The door is mechanically connected to the control means such that the door can be opened and closed (as shown in FIG. 6) via the control means. Preferably, the slidable connection and control means are configured to allow the door to "open" fully to allow unobstructed access to the notch for placement of the "taco" folded, inside end of the cannula, and allows for the user to vary the position of the door to increase or decrease tension on the neck of the cannula when the cannula is inserted in the cannula holder. However, the door may also be fixed into place at one or more positions, resulting in a slotted type cannula holder that is adjustable to accommodate different sized cannulas. The door should be curved, following the curvature of the circumference of the tubular cannula, or may be essentially flat.

In some implementations, the door may have a "V" or "U" shaped notch at one end of the door or in the notch itself in which the cannula can be fixed. In some implementations, "V" or "U" shaped notch may be textured, ramped, have "wings," or have an overhang (as described above) to facilitate folding and placement of the cannula in the cannula holder. Exemplary implementations are illustrated in FIG. 6.

To insert a flexible button style cannula using a tubular insertion device having a sliding cannula holder in accordance with the present invention, a surgical guide is placed in an incision using known methods, such as a cannulated switching stick. A flexible button style cannula is placed in the notch of the tubular insertion device by folding the flange of the cannula, tucking it into the notch of the cannula holder door, and using the control means to manipulate the door such that the door places tension on the neck and/or inner flange of the cannula. The surgical guide is then inserted into the conduit of the tubular insertion device, the insertion device is inserted into the portal to a desired depth, and then the door is opened via the control means. When the cannula is released from the insertion device (confirmed via a visualization device), the surgical guide and insertion device are removed, and the flexible cannula returns to its non-deformed shape and fits snuggly against the tissues surrounding the portal. It should be appreciated that, in some situations, it may be necessary to further manipulate the cannula before withdrawing the tubular insertion device. To accomplish this, a portion of the cannula may be grasped between the door and the notch by aligning a portion of the cannula with the notch in the insertion device, and then manipulating the door via the control means to place tension on the "caught" portion of the cannula.

Blade-Type Inserter

As illustrated in FIG. 7, an inserter in accordance with the present invention has an insertion tip 710 that is connected to a substantially flat (substantially rectangular in cross-section) elongated linear body 720.

It should be appreciated that a device having a substantially rectangular cross section may have one or more sides that are at least slightly curved, with sides meeting to form approximately 90 degree angles. A cannula holder 735, as described with respect to the tubular insertion device, is located along the substantially flat elongated linear body 720, proximal to the insertion tip 710. A control means 740 for the insertion device and/or the cannula holder is located at the proximal end of the elongated body 720. The various control means are described with respect to the tubular insertion device. Insertion devices in accordance with this embodiment are referred to herein as a "blade-type inserter."

The insertion tip 810 of the blade-type inserter may have a blunt, rounded shape (as shown in FIGS. 8(*a*) and 8(*b*)) at the distal end, an asymmetrical, tapered shape (as shown in FIGS. 8(*c*) and 8(*d*)) at the distal end. In some embodiments, the insertion tip and elongated body may be continuous. In some embodiments, the insertion tip may be rigid. In other embodiments, the insertion tip may be flexible.

A cannula holder is located along the elongated body proximal to the insertion tip. The cannula holder may be a slotted cannula holder, a pivoting cannula holder, a sliding cannula holder, or any combination thereof without departing from the scope of the invention. These various cannula holders may be adapted for use with a flat, linear elongated body having a rectangular cross-section. "Opening" and "closing" of the cannula holder is controlled by a user (surgeon) via control means, when aspects of cannula holder are movable. It should also be appreciated that an adjustable cannula holder may also be fixed in the open position.

In some embodiments, the control means for the cannula holder permits bi-directional (opening and closing) control of the cannula holder. In a non-limiting example, the control means for the cannula holder may be finger-loop ratcheting handles located at the proximal end of the insertion device. In some embodiments, the control means for the cannula holder may include a locking mechanism or a self-releasing lock mechanism. Further, in some embodiments, the control means for the cannula holder may be combined with the control means for the insertion device and include two handles; one of which is stationary to facilitate manipulation of the entire insertion device, and the other handle being movable and permitting a user to release and secure the releasable mechanical mechanism. Preferably, the control means for the cannula holder permits a user (surgeon) to control and vary the amount of tension placed on the neck of the cannula. In another embodiment, a control means has a thumb pad that is controlled by the thumb such that, when an overhand grip is placed on the handle the thumb can move the thumb control mechanism distal to release the restraint mechanism and proximal to secure it. In still other embodiments, the control means may include one or more motors operable to open and close the cannula holder via input from an input device such as a track pad or joystick-style input device. In some embodiments, for example where the cannula holder is not movable, separate control means for the cannula holder is not necessary, and the control means for the insertion device is a handle or grip used to manually manipulate the inserter, and may be further adapted to provide ergonomic advantages for a user. It should be appreciated that any known control means for surgical tools or the like may be implemented for control of the cannula holder and/or insertion device without departing from the scope of the invention.

Slotted Cannula Holder

A slotted cannula holder includes an elongated opening, between the proximal end of the insertion tip and the distal end of the elongated body, that extends the full depth/thickness of the blade-type inserter. The elongated opening may be adjustable or fixed, as described with respect to the tubular insertion device. FIGS. 8(*a*)-8(*d*) illustrate a blade-type inserter having an adjustable slotted cannula holder. The insertion tip and the elongated linear body are connected via a mechanical mechanism, such as a uni-directional or bi-directional ratchet mechanism, threaded rods, or the like, and the mechanical mechanism is configured to allow the user (surgeon) to vary distance between the proximal end of the insertion tip and the distal end of the elongated body and, thus, vary the size in the opening that is configured to accommodate a flexible cannula. In some implementations, the mechanical mechanism may be driven by one or more motors and may be controlled by a computer or trigger mechanism. Preferably, at least a portion of the mechanical mechanism provides structural rigidity so that the slotted cannula inserter does not deform under the pressure of insertion or removal. The mechanical mechanism is configured to be controlled by the control means described above.

Another exemplary blade-type inserter having a fixed slotted cannula holder is illustrated in FIGS. 8(*e*) and 8(*f*). In this exemplary embodiment, cannula 850 is folded or deformed in order to fit through the slotted cannula holder 835 and, as illustrated in FIGS. 8(*e*) and 8(*f*), returns to its original shape, which assists in holding the flexible cannula in place in the slotted cannula holder. In use, a user grasps the control means/end of the blade-type inserter, and the insertion tip 810 is used to guide the blade-type inserter into the portal, and the slotted cannula holder retains the flexible cannula as it is inserted through the portal. Once at least one end of the cannula is inserted through the portal, the blade-type inserter is manipulated by the user via the control means to release the flexible cannula holder from the slot. Preferably, release of the cannula can be confirmed using a visualization device. Once the cannula is released, the blade-type inserter can be removed from the portal without disturbing the position of the cannula. In this exemplary implementation, the control means (not shown) is a handle or grip used to manipulate the elongated body and slotted cannula holder of the blade-type inserter.

In some implementations, a conduit for a surgical guide, such as a guide wire, may be located along the length of one side of the blade-type inserter, for example, along a portion of the mechanical mechanism. In still other implementations, a conduit for a surgical guide is located on either or both of the insertion tip and/or elongated body, and the surgical guide serves as a folding guide for the inner flange of the flexible cannula.

In use, the blade-type inserter having an adjustable slotted cannula holder is inserted by placing a cannula in the opening such that the flanges are fully expanded, and securing the cannula in the opening with one flange on each side of the opening. The cannula is secured in the opening by engaging the releasable mechanical means via the control means, if such releasable mechanical means is included, and then inserting the blade type inserter in the portal, with or without use of the surgical guide. The flexibility of the cannula allows for deformation as the cannula is inserted. Once the blade-type inserter is inserted to the desired depth, the blade-type inserter is manipulated using the external end. If a releasable mechanical means is included, it is expanded using the mechanical mechanism. After release of the cannula from the blade-type insertion device is confirmed via a visualization device, the blade-type inserter is removed. It should be appreciated that the position of the cannula may need to be adjusted one or more times before the blade-type inserter is removed. In some embodiments, this is accomplished by opening the adjustable cannula holder via the control means, grasping a portion of the cannula in the opening, closing the adjustable cannula holder via the control means, and adjusting the position of the cannula and blade-type inserter using the visualization means for guidance.

Pivoting Cannula Holder

A blade type inserter having a pivoting cannula holder, as illustrated in FIGS. 9(*a*)-9(*f*) includes a pivoting door located along one face of the flat elongated body of the blade-type inserter, proximal to the insertion tip. The insertion tip 910 may be blunt and/or tapered, and may be centered or offset relative to the flat elongated body of the inserter. As illustrated in FIGS. 9(*a*) and 9(*b*), a partial-width notch is formed along one side of the flat elongated body. The partial-width notch is preferably configured to accommodate at least a portion of a flexible cannula intended to be inserted in a body. As illustrated in FIGS. 9(*d*) through 9(*f*), a partial or full depth notch is formed on the top (or bottom) of the flat elongated body. No matter which face of the blade-type inserter the notch is formed in, a door 930 extending at least a portion of the length of the notch is pivotably connected to the flat elongated body at one end of the notch via, for example, a hinge 940. While FIGS. 9(*a*) and 9(*b*) illustrate an example in which the pivotable connection is located at the proximal end of the notch, the pivotable connection may, in some embodiments, be located at the distal end of the notch, as illustrated in FIGS. 9(*d*) through 9(*f*).

The door may extend along the entire length of the notch (as shown in FIGS. 9(*a*) through 9(*c*)), or may extend along a portion of the length of the notch (as shown in FIGS. 9(*d*) through 9(*f*). The pivotable connection is configured to be controlled via the cannula holder control means such that the grasper door 930 can be opened (as shown in FIGS. 9(*a*), 9(*d*), and 9(*f*)) and closed (as shown in FIGS. 9(*b*) and 9(*e*)). Preferably, the pivotable connection and cannula holder control means are configured to allow the grasper door to "open" fully to allow unobstructed access to the notch for placement of the neck of a cannula or "taco" folded inside end of the cannula, and also to allow for the user to vary the position of the door to increase or decrease tension on the neck of the cannula when the cannula is inserted in the grasper cannula holder. In some implementations, placing sufficient tension on the cannula may require that the door be capable of pivoting beyond the "closed" position and into the interior of the notch. In a non-limiting example, the position of the door may be controlled by a ratchet mechanism. In some embodiments, the door extends the entire depth of the flat elongated body such that, when the door is completely closed (as in FIG. 9(*c*)), the side (or top) of the elongated body appears as a continuous surface.

In some embodiments, as illustrated in FIG. 10, the door may be curved or shaped to accommodate the item it is intended to hold and, further, may extend in the distal direction to form at least a portion of the insertion tip 1010. In other embodiments, as shown in FIGS. 10(*a*)-10(*d*), the entire insertion tip is formed from two doors 1030 that can be manipulated to open and close.

In some embodiments, the door may have a "V" or "U" shaped notch at the "free" end to facilitate grasping of a cannula. In some embodiments, the distal end of the grasper door and/or the distal end of the notch may be textured, ramped, or have an overhang (as described above) to facilitate folding and placement of the cannula in the cannula holder.

To insert a flexible button style cannula using a blade-type inserter having a pivoting cannula holder in accordance with the present invention, a flexible button style cannula is placed in the notch of the tubular insertion device by folding the flange of the cannula, tucking it into the notch of the cannula holder, and using the control means to manipulate the door such that the door places tension on the neck and/or inner flange of the cannula. The insertion device is then inserted into the portal to a desired depth, and then the door is opened via the control means. When the cannula is released from the insertion device (confirmed via a visualization device), the surgical guide and insertion device are removed, and the flexible cannula returns to its non-deformed shape and fits snuggly against the tissues surrounding the portal. It should be appreciated that, in some situations, it may be necessary to further manipulate the cannula before withdrawing the tubular insertion device. To accomplish this, a portion of the cannula may be grasped between the door and the notch by aligning a portion of the cannula with the notch in the insertion device, and then manipulating the door via the control means to place tension on the "caught" portion of the cannula.

Sliding Cannula Holder

Figure 11A:
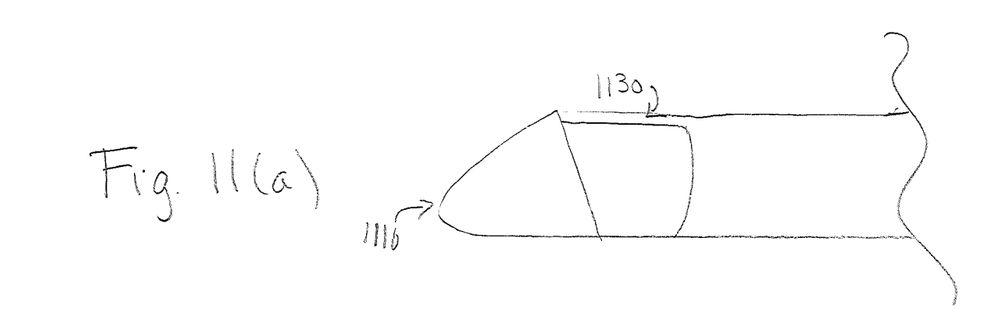
FIGS. 11(a) and 11(b) illustrate a blade-type inserter having a sliding cannula holder in accordance with the present invention.
Figure 11B:
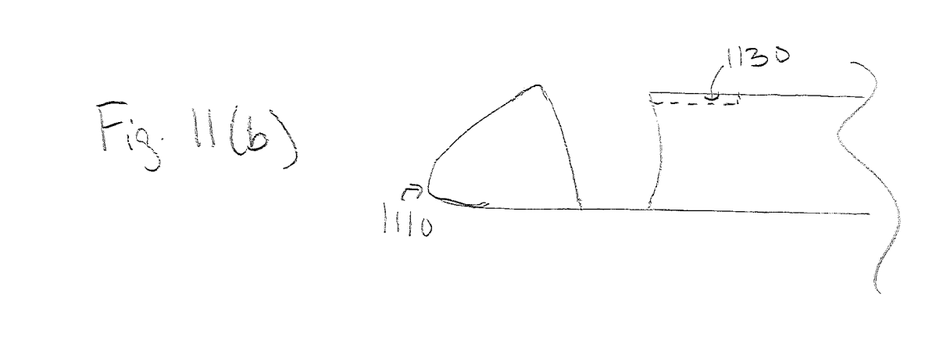

A sliding cannula holder is located along one face of the flat elongated body of the blade-type inserter, proximal to the insertion tip, as illustrated in FIGS. 11(a) and 11(b). While the exemplary implementation presented herein is described with respect to one of the side faces, a sliding cannula holder could also be located on the top or bottom surface without departing from the scope of the invention. The insertion tip 1110 may be blunt and/or tapered, and may be centered or offset. As illustrated in FIGS. 11(a) and 11(b), a partial-width notch is formed in the interior of the side of the flat elongated body. The partial-width notch is preferably configured to accommodate at least a portion of a flexible cannula intended to be inserted in a body, and the notch may be shaped, for example with a ramp, taper, V-lock, or the like, to accommodate a flexible cannula. A door 1130 is slidably connected to the proximal end of the elongated body such that the door can be advanced in the distal direction to close the opening of the notch via the cannula holder control means.

In some implementations, for example where the sliding door is located on the top or bottom of the blade-type inserter, the end of the door that contacts the cannula may be shaped, having a notch, V-lock, or the like, to facilitate securing and placing the cannula.

To insert a flexible button style cannula using a blade-type inserter having a sliding cannula holder in accordance with the present invention, a flexible button style cannula is placed in the notch of the blade-type inserter such that the neck of the cannula is in the notch, and the door is closed via control means such as a sliding rod with a thumb pad. The insertion device is then inserted into the portal to a desired depth, and then the sliding door is opened via the control means. When the cannula is released from the insertion device (confirmed via a visualization device), the surgical guide and insertion device are removed, and the flexible cannula returns to its non-deformed shape and fits snuggly against the tissues surrounding the portal. It should be appreciated that, in some situations, it may be necessary to further manipulate the cannula before withdrawing the blade-type inserter. To accomplish this, a portion of the cannula may be grasped between the door and the notch by aligning a portion of the cannula with the notch in the insertion device, and then manipulating the door via the control means to place tension on the "caught" portion of the cannula.

While the foregoing describes preferred embodiments of the invention, variations can be made without departing from the scope of the invention. For example, the orientation of any of the doors of the various cannula holding mechanisms disclosed herein may be varied without departing from the scope of the invention. The instruments and methods described herein may also be used in conjunction with any deformable instrument, tool, or device to facilitate placement and/or deployment of the deformable instrument, tool, or device in a small space or through a small space, such as a small incision or a hole drilled in bone.

What is claimed is:

1. A cannula insertion device, comprising:
    a rigid elongated body having a length that extends from a first end to a second end, the rigid elongated body having a substantially rectangular cross section that defines a width and a depth of the rigid elongated body;
    a tapered insertion tip located at the first end of the elongated body;
    an elongated opening along at least one face of the rigid elongated body between the insertion tip and second end, the elongated opening having a longer dimension and a shorter dimension, wherein
        the elongated opening is oriented such that the longer dimension extends along the length of the rigid elongated body and the shorter dimension extends along the width of the rigid elongated body,
        the elongated opening extends through the depth of the elongated body and is configured to receive a cannula that is at least partially deformable, and
        the shorter dimension of the elongated opening is smaller than a diameter of the cannula in an undeformed state; and
    cannula insertion device control means located at the second end of the rigid elongated body.

2. A cannula insertion device according to claim 1, wherein the longer dimension of the elongated opening is fixed.

3. A cannula insertion device according to claim 1, wherein the longer dimension of the elongated opening is adjustable.

4. A cannula insertion device according to claim 3, further comprising cannula holder control means.

5. A cannula insertion device according to claim 1, wherein the insertion tip is blunt.

6. A cannula insertion device according to claim 1, wherein the insertion tip is tapered to facilitate insertion into a portal.

7. A cannula insertion device according to claim 1, wherein the insertion tip is blunt and tapered to facilitate insertion into a portal.

8. A system for facilitating access to a surgical site via minimally invasive means, comprising:
    a rigid elongated body having a length that extends from a first end to a second end, the rigid elongated body having a substantially rectangular cross section that defines a width and a depth of the rigid elongated body;
    a tapered insertion tip located at the first end of the elongated body;
    an elongated opening along at least one face of the rigid elongated body between the insertion tip and second end, the elongated opening having a longer dimension and a shorter dimension, wherein
        the elongated opening is oriented such that the longer dimension extends along the length of the rigid elongated body and the shorter dimension extends along the width of the rigid elongated body, the elongated opening extends through the depth of the elongated body and is configured to receive a cannula that is at least partially deformable, and the shorter dimension of the elongated opening is smaller than a diameter of the cannula in an undeformed state; and cannula insertion device control means located at the second end of the rigid elongated body; and a cannula having a deformable flange at one end.

9. The system according to claim 8, wherein the longer dimension of the elongated opening is fixed.

10. The system according to claim 8, wherein the longer dimension of the elongated opening is adjustable.

11. The system according to claim 8, further comprising cannula holder control means.

12. The system according to claim 8, wherein the insertion tip is blunt.

13. The system according to claim 8, wherein the shorter dimension of the elongated opening is smaller than the diameter of the flange of the cannula.

14. The system according to claim 8, wherein the insertion tip is tapered to facilitate insertion into a portal.

15. The system according to claim 8, wherein the insertion tip is blunt and tapered to facilitate insertion into a portal.

* * * * *